United States Patent [19]

Kolobow

[11] Patent Number: 5,305,740

[45] Date of Patent: Apr. 26, 1994

[54] SEALING MEANS FOR ENDOTRACHEAL TUBES

[75] Inventor: Theodor Kolobow, Rockville, Md.

[73] Assignee: The United States of America as represented by the Secretary of the Department of Health and Human Services, Washington, D.C.

[21] Appl. No.: 878,784

[22] Filed: May 6, 1992

Related U.S. Application Data

[63] Continuation-in-part of Ser. No. 758,824, Sep. 12, 1991.

[51] Int. Cl.⁵ ............................................. A61M 16/00
[52] U.S. Cl. ........................... 128/207.14; 128/207.15; 604/278
[58] Field of Search ................... 604/278; 128/207.14, 128/207.15, 658, 220.24; 264/310

[56] References Cited

U.S. PATENT DOCUMENTS

| | | | |
|---|---|---|---|
| 724,913 | 4/1903 | Montgomery | 604/278 |
| 5,090,408 | 2/1992 | Spofford | 128/207.14 |
| 5,096,454 | 3/1992 | Samples | 604/54 |

*Primary Examiner*—Edgar S. Burr
*Assistant Examiner*—Eric P. Raciti
*Attorney, Agent, or Firm*—Lowe, Price, LeBlanc & Becker

[57] ABSTRACT

A sealing element for a tubular member such as an endotracheal tube which includes a circular collar portion and a pliable flange or gill. One or more of the sealing elements are positioned on a tubular member such as an endotracheal tube. When the tubular member is inserted into a lumen such as a trachea, the pliable flange(s) or gill(s) forms a seal between the outer wall of the tubular member and the inner wall of the lumen. In the case of endotracheal tubes the sealing elements replace conventional inflatable cuffs and allow for tubes having diameters less than 5 mm.

15 Claims, 5 Drawing Sheets

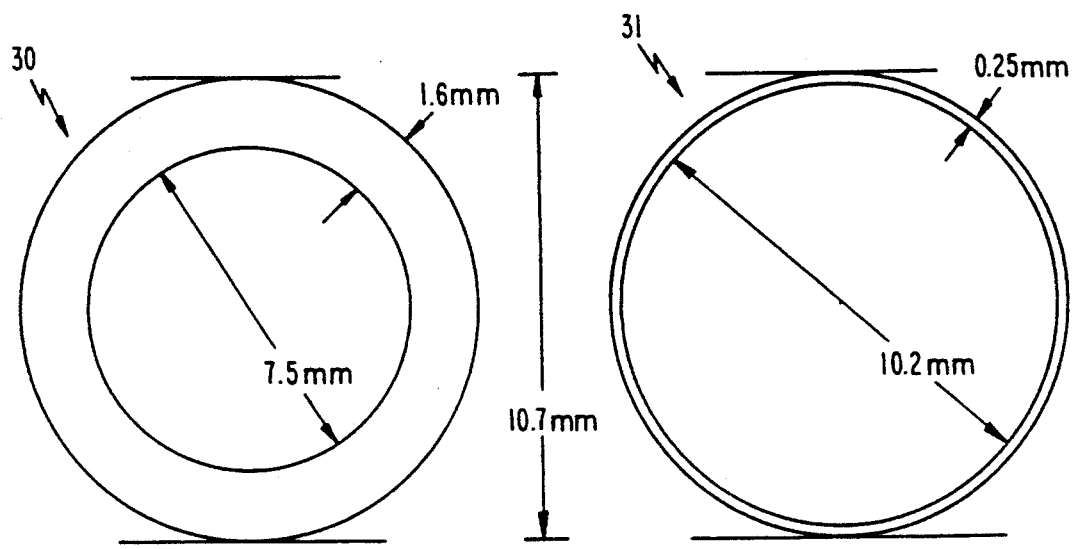
FIG. 2A
PRIOR ART
FIG. 2B
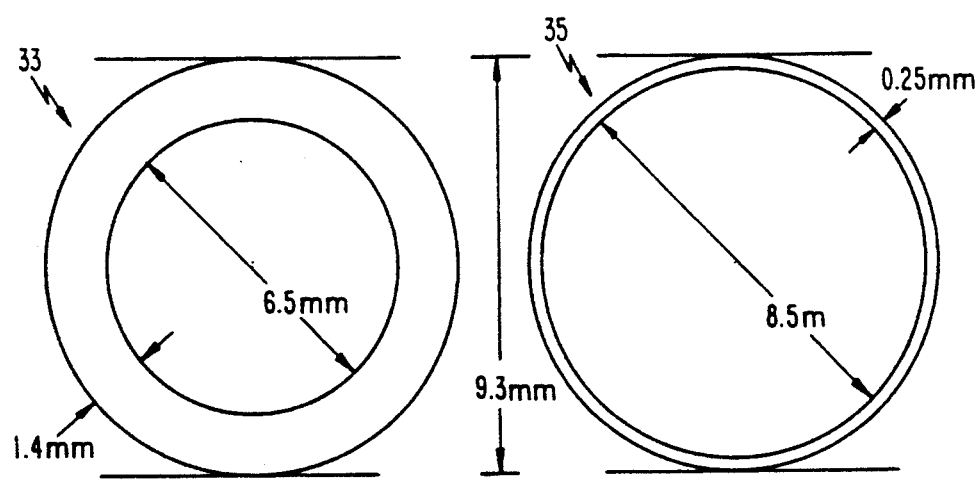
FIG. 3A
PRIOR ART
FIG. 3B

SEALING MEANS FOR ENDOTRACHEAL TUBES

RELATED APPLICATIONS

This application is a Continuation-In-Part of Application Ser. No. 07/758,824, filed Sep. 12, 1991, the complete disclosure of which is expressly incorporated herein by reference.

FIELD OF INVENTION

The present invention is directed to endotracheal tubes, their use and fabrication. More particularly, the present invention is directed to a novel seal means for endotracheal and similar tubes which seal means effectively provides a fluid seal between the outer wall of the tube and the lumen into which the tube is to be inserted.

The present invention is further directed to the novel seal means used in conjunction with an ultra thin walled wire reinforced endotracheal tubing. The ultra thin walled tubing comprises a polymer tube having incorporated therewith a stainless steel spring material.

BACKGROUND ART

Endotracheal tubes are widely used in anesthesia and critical care medicine. In use, endotracheal tubes provide access to the upper airways for controlled, assisted ventilation or spontaneous unassisted ventilation with positive end expiratory pressure.

One of the drawbacks of inserting an endotracheal tube into an upper airway of a patient results in the reduction of the lumen of the airway. One cause by which the lumen is reduced is the inability to use the largest possible endotracheal tube for a given patient without subjecting the patient to increased risks. Generally, it is not advisable to insert the largest possible endotracheal tube in a patient since such an attempt will entail many trials and errors which may take additional time which should be avoided especially in critical care or emergency situations.

In addition, the wall thickness of an endotracheal tube needs to be such to provide sufficient strength so as to be safely handled by the using physician or technician during insertion and to maintain the tube stable after insertion. At present, adult endotracheal tubes range between 7 to 9 millimeters in internal diameter with a total wall thickness ranging between 1.4 and 1.5 millimeters. For newborn endotracheal tubes, the decrease in lumen internal diameter as a result of the required wall thickness amounts to approximately 0.5 millimeters or more.

Any decrease in the lumen due to wall thickness of an endotracheal tube has a profound effect on the airway resistance, since the resistance to air flow is inversely proportional to the fourth power of the radius.

As a result of the deficiencies in prior art endotracheal tubes, a need has developed to provide an endotracheal tube having reduced airway resistance so as to facilitate establishment of artificial airways other than those using mechanical ventilators.

Conventional technology used in the fabrication of blood catheters uses either extrusion or dip coating onto mandrels. Extrusion technology has the advantage of low cost, but has little flexibility. With extrusion, the resulting thin wall catheters are rather stiff and are liable to kink or bend and thus obstruct the inner passageway. The dip coating technique used for currently available catheters and tubes is not reproducible in thin wall gauges and, therefore, wall thickness remain substantial.

For successful use, it is important to provide a good seal between the outer wall of an endotracheal tube and the tracheal into which it is inserted. Conventionally, such a seal is provided by using an inflatable cuff attached to the endotracheal tube. Such inflatable cuffs utilize either low or high pressure fluids to cause them to inflate and thus require additional fluid passageways that are connected to the inflatable cuffs.

Unfortunately, the use of inflatable cuffs is sometimes injurious to the tracheal, causing pressure necrosis, bleeding, fistula formation, etc. Following removal of endotracheal tubes having inflatable cuffs, particularly following long term use, there is a significant potential for scar formation with resultant tracheal stenosis. Because of the above sequelae, the use of inflatable cuffs is frowned on in conjunction with newborns and small children, because such adverse effects oftentimes are far more debilitating were they to occur in patients other than adults.

As a result of the above problems and concerns and design limitations, endotracheal tubes up to size 5 mm do not presently employ inflatable cuffs. As an adverse side effect to this accepted design which lacks a sealing means, there is likely to be a significant air leak that can at times be very troublesome.

The present invention provides an ultra thin walled wire reinforced endotracheal tube which provides reduced airway resistance to permit easier breathing by a patient. The ultra thin walled endotracheal tube comprises a polymer having incorporated therewith a stainless steel spring material to form a continuous tubing. The combination of the polymer and stainless steel spring material provides an ultra thin wall of the tubing which permits the use of an endotracheal tube having similar diameters as prior art tubings but with increased internal diameters and resultant reductions in airway resistance.

The present invention further provides a novel sealing means which avoids the use of inflatable cuffs, and which is applicable to endotracheal and similar tubes of all sizes including those having an outside diameter which is less that about 5 mm.

SUMMARY OF THE INVENTION

It is accordingly an object of the present invention to provide a sealing means for endotracheal and similar tubes which are designed to be inserted and sealed in a lumen.

Another object of the present invention is to provide endotracheal and similar tubes which have sealing means on outer walls thereof.

A further object of the present invention is to provide ultra thin walled wire reinforced endotracheal tubing having sealing means on an outer wall thereof.

It is a further object of the present invention to provide an apparatus for and a method of making ultra thin walled wire reinforced endotracheal tubing having sealing means on an outer wall thereof.

It is a still further object of the present invention to provide sealing means on endotracheal and similar tubes which have outside diameters of less than about 5 mm.

It is a yet further object of the present invention to provide endotracheal tubing which is particularly useful in conjunction with newborn, infants and children.

In accordance with these and further objects of the invention which will become apparent as the disclosure thereof is presented below, the present invention provides a sealing means for a tubular member which comprises a circular collar portion having a through hole centrally located therein and a pliable flange attached to an outer circumferential surface of the circular collar portion, the pliable flange being continuous along the entire circumferential surface of the circular collar portion.

The present invention further provides for a device comprising a tubular member and a sealing means provided on the tubular member, the sealing means including a circular collar portion having a through hole centrally located therein and a pliable flange attached to an outer circumferential surface of the circular collar portion, the pliable flange being continuous along the entire circumferential surface of the circular collar portion.

In addition, the present invention provides an endotracheal tube comprising a tubular member and a sealing means on the tubular member, the sealing means including a circular collar portion having a through hole centrally located therein and a pliable flange attached to an outer circumferential surface of the circular collar portion, the pliable flange being continuous along the entire circumferential surface of the circular collar portion.

BRIEF DESCRIPTION OF DRAWINGS

The present invention will be described with reference to that attached drawings which are given by way of non-limiting examples only, in which:

FIG. 2A shows an end view of a prior art endotracheal tube;

FIG. 2B shows an end view of an endotracheal tube according to the present invention;

FIG. 3A shows an end view of another prior art endotracheal tube;

FIG. 3B shows an end view of a smaller size ultra thin walled wire reinforced endotracheal tube of the present invention;

DESCRIPTION OF THE PREFERRED EMBODIMENTS

The present invention is concerned with endotracheal tubes which provide artificial airways in applications such as anesthesia and critical medicine. According to one embodiment, the present invention provides ultra thin walled wire reinforced endotracheal tubes which offer advantages over prior art tubing by providing, for the same outer diameter of tubing, an increased inner diameter and reduced airway resistance. By incorporating a stainless steel spring material with a polymeric material in a thin walled tubing configuration, an endotracheal tube is provided which has sufficient strength to be safely handled by a user.

By providing low air resistance endotracheal tube, whereby patient breathing is made easier, patients may be able to utilize a simpler means of respiratory assistance such as continuous positive airway pressure (CPAP) rather than mechanical ventilation means.

In the newborn patient population, the lowering of airway resistance is of vital importance since newborns are more likely to become exhausted or have further difficulty in breathing by using prior art endotracheal tube having significant airway resistance. By utilizing the inventive ultra thin wall wire reinforced endotracheal tubes in newborn patient application, significant reductions in airway resistance are attainable.

In addition, developments and other alternatives for mechanical ventilation such as intratracheal pulmonary ventilation which include a reduction in dead space ventilation and a decrease in airway pressure favor the utilization of establishment of artificial airways having reduced resistance to air flow. As will be described hereinafter, the inventive tubing reduces the wall thickness by 50–80%, thereby resulting in a two- to four-fold decrease in air flow resistance.

The present invention is also directed to a sealing means for endotracheal and similar tubes which are designed to be inserted into a lumen and sealed therein to provide a fluid flow passage. For example, in addition a to being useful in conjunction with endotracheal tubes, the sealing means of the present invention could also be used in conjunction with ureteral catheters and similar devices.

As discussed in detail below, the sealing means of the present invention includes one or more thin, soft, pliable gills or flanges which are provided on the outer wall of a tubular member such as an endotracheal tube. The gills or flanges are sufficiently flexible to form a fluid tight seal between the outer wall of the tubular member and the corresponding or adjacent inner wall of a lumen into which the tubular member is inserted and positioned. The gills or flanges are made of a suitably pliable material such as polyvinyl chloride, silicone rubber, polyethylene, and the like, which are biocompatable for their intended use.

Figure 1:
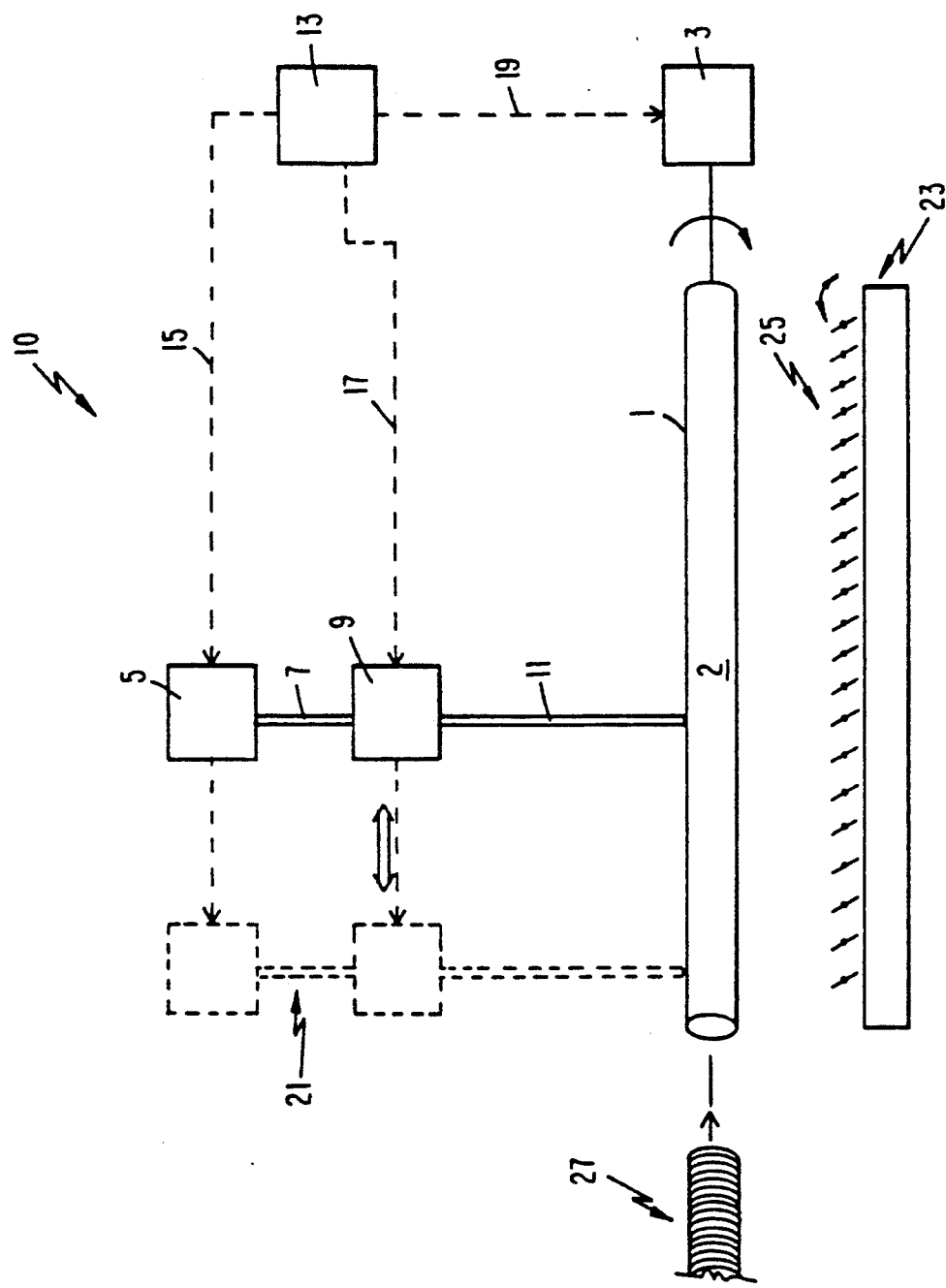
FIG. 1 shows a schematic representation of one embodiment of the apparatus utilized for making the ultra thin walled wire reinforced endotracheal tubing.

With reference now to FIG. 1, a schematic representation of an apparatus adapted for making ultra thin walled wire reinforced endotracheal tube is illustrated. The apparatus is generally designated by the reference numeral 10 and is seen to include a cylindrical mandrel 1 having a release agent coating on the surface 2 thereof. The release agent 2 is designed to facilitate removal of the ultra thin walled wire reinforced endotracheal tubing from the cylindrical mandrel 1. The release agent may be any agent known in the art such as Teflon ®. The cylindrical mandrel may be made of any material having sufficient strength to provide support for the tubing, preferably a steel rod.

The cylindrical mandrel is connected to a lathe means 3 which includes drive means therewith to rotate the mandrel at a predetermined speed. Of course, any known means capable of rotating a cylindrical mandrel may be utilized in substitution for the lathe 3.

The apparatus for making the ultra thin walled wire reinforce endotracheal tubing also includes a polymer source means 5 which supplies a dissolvable polymer such as polyurethane Lycra ® under pressure to a metering pump 9 via the line 7. The polymer source means may be a closed container including a source of inert gas to provide the pressure to supply the dissolved polymer to the metering pumping 9. Preferably, the source of the pressure is a dry nitrogen or other inert gas.

The metering pump 9 includes a nozzle 11 made out of a flexible tubing such as Teflon ®. The tubing 11 should have sufficient flexibility and thickness to follow the contours of the cylindrical mandrel 1 and float on the polymer layer as it emerges from the nozzle. The flexibility of the tubing 1 may be enhanced by the addition of a spring material surrounding the tubing. The metering pump 9 may be a gear fluid pump designed to meter a solution of polymer onto the mandrel.

The polymer source means 5 and metering pump means 9 also include a cross feed means which permits the source means 5, metering means 9 and nozzle 11 to traverse the length of the mandrel 1. As illustrated by the reference numeral 21 in FIG. 1, the source means 5, metering pump 9 and nozzle 11 are displaced along the longitudinal axis of the cylindrical mandrel 1. The longitudinal movement of the nozzle 11 permits that polymer to be continuous applied to the mandrel over a preselected pattern.

A control means 13 is provided that regulates the deposition of the polymer on the mandrel 1. The control means is connected to the polymer source means 5 via the line 15, the metering pump 9 via the line 17 and the lathe 3 via the line 19. By controlling the rotation of the mandrel 1 via the lathe 3 and the amount of polymer deposited on the mandrel 1, the thickness of polymer applied to the mandrel or wall thickness of the ultra thin walled and wire reinforced endotracheal tubing may be controlled and varied. The control means 13 also provides control over longitudinal traversing of the nozzle 11 and associated components and the cylindrical mandrel 1. It should be understood that, although the nozzle 11, metering pump 9 and polymer source means 5 are depicted as longitudinally traversing the length of the cylindrical mandrel 1, in another embodiment, the polymer source means 5 may be stationery with the metering pump 9 and nozzle 11 traversing the length of the mandrel 1. It should be understood that the mechanism for providing the longitudinal traversing movement of either the metering pump 9 and nozzle 11 or these components with the polymer source means 5 are well recognized in the prior art. For example, these components may be longitudinally traversed using a drive means and rack and pinion gearing.

The apparatus 10 also includes a heating means 23 which supplies heat such as hot air to the mandrel 1 to dry the polymer solution after deposition on the mandrel.

The heating means may a strip heater or other known heating means. The heating means 23 may also include individually adjustable baffles 25 which facilitate directing the hot air toward the mandrel 1. The adjustable feature of the baffles 25 permit varying the amount of drying air along the length of the mandrel 1. For example, when producing a tapered endotracheal tube, certain areas of the tube having increased wall thickness require a higher heat input for drying purposes. In this situation, the individually adjustable baffles are arranged to direct more hot air to the portion of the cylindrical mandrel having the endotracheal tube with increased wall thickness.

FIG. 1 also depicts a coil spring 27 which is designed to be inserted over the Teflon ® coated cylindrical mandrel 1. The spring 27 may be manually inserted over the rod or, alternatively, by known mechanical means. As an alternative embodiment, the spring material may be in the form of an unwound wire or flat material and be wound around the cylindrical mandrel in a known fashion. As will be described hereinafter, the spring 27 may be applied to the mandrel 1 after or during the deposition of the polymeric material.

The method of making the ultra thin walled wire reinforced endotracheal tubing will now be described. In the first embodiment, a polymeric material such as a polyurethane Lycra ® is dissolved in a compatible solvent. A typical concentration of polymeric material would range between 25–28 weight percent polymer in the solvent. This range is only exemplary and more or less concentrations of polymeric material may be utilized depending on the particular polymer being employed. The dissolved polymer is supplied to a metering pump under pressure such as dry nitrogen. The metering pump, such as a fluid gear pump, meters the dissolved polymer unto the rotating surface of the mandrel while the nozzle traverses the length of the cylindrical mandrel. The deposited polymer is permitted to air dry, or alternatively, dry by application of a source of heat such as a strip heater or the like. This sequence may be repeated if an increased thickness of polymeric material is desired on the surface of the cylindrical mandrel.

By choosing a particular rate of deposition of polymeric material, the solvent evaporation rate can be optimized such that one layer of polymer can be deposited onto the previously deposited and dried layer to build up thickness. In a further embodiment, successive deposition of several layers of polymeric solution may be performed while traversing the cylindrical mandrel on a single run. In this embodiment, a plurality of nozzles may be utilized which are spaced apart from each other such that following nozzles are depositing polymeric material to an already dried polymeric material layer.

Once the initial layer or layers of polymeric solution are deposited on the cylindrical mandrel a spring material, preferably a stainless steel spring, is applied to the cylindrical mandrel. In one embodiment, the stainless steel spring may be in an uncoiled configuration, either flat or round in size, and wound around the polymer-coated mandrel by known mechanical means. Alternatively, the stainless steel spring may be provided in a pre-coiled configuration and inserted over the mandrel.

The choice of winding per inch for the spring or the diameter or cross-sectional area of the spring material may vary depending upon the desired spring properties and flexibility of the ultra thin walled wire reinforced endotracheal tube. Furthermore, it should be understood that the spring material cross-sectional area, or diameter if the spring material is round, is sized to provide the ultra thin walled wire reinforced endotracheal tubing having a reduced wall thickness while maintaining sufficient strength to avoid kinking or bending during handling and subsequent constriction of an airway passage.

Once the spring wire is applied to the mandrel, further deposition of polymeric material may be performed to yield a smooth outside surface having the desired final diameter.

In a further embodiment, the spring material may be wound around the mandrel or inserted thereover, simultaneously with the application of the polymer solution.

After the polymer has been applied, the sealing means described below is positioned on the form polymer tubing either before or after the tubing is removed from the mandrel. The sealing means are fixed to the tubing by means of a suitable, biocompatable cement, selected from those known in the art. According to another embodiment, the sealing means may be positioned on the tubular member prior to complete curing of the polymer. Thereafter, the curing of the polymer may be used to secure the sealing means. Other suitable means such as welding or heat sealing the sealing means on the tubular member could also be used.

With reference to FIGS. 2A and 2B, a comparison is illustrated between prior art endotracheal tubes and the ultra thin walled wire reinforced endotracheal tubing of the present invention. As can be seen from FIG. 2A, the prior art endotracheal tube having an outer diameter of 10.7 millimeters has an inner diameter of 7.5 millimeters due to the wall thickness of 1.6 millimeters. In contrast, the ultra thin wall wire reinforced endotracheal tubing of the present invention may be made having the same outer diameter of 10.7 millimeters but with an increased inner diameter of 10.2 millimeters as a result of the reduced wall thickness of 0.25 millimeters.

Referring to FIGS. 3A and 3B, a similar comparison is made wherein the prior art endotracheal tubing 33 is compared to the ultra thin walled wire reinforced endotracheal tubing 35 of the present invention. In this manner, the prior art endotracheal tubing 33 having an outer diameter of 9.3 millimeters has an inner diameter of 6.5 millimeters. The ultra thin walled wire reinforced endotracheal tubing 35 has an increase in the inner diameter to 8.8 millimeters for the same 9.3 millimeter outside diameter.

Figure 4:
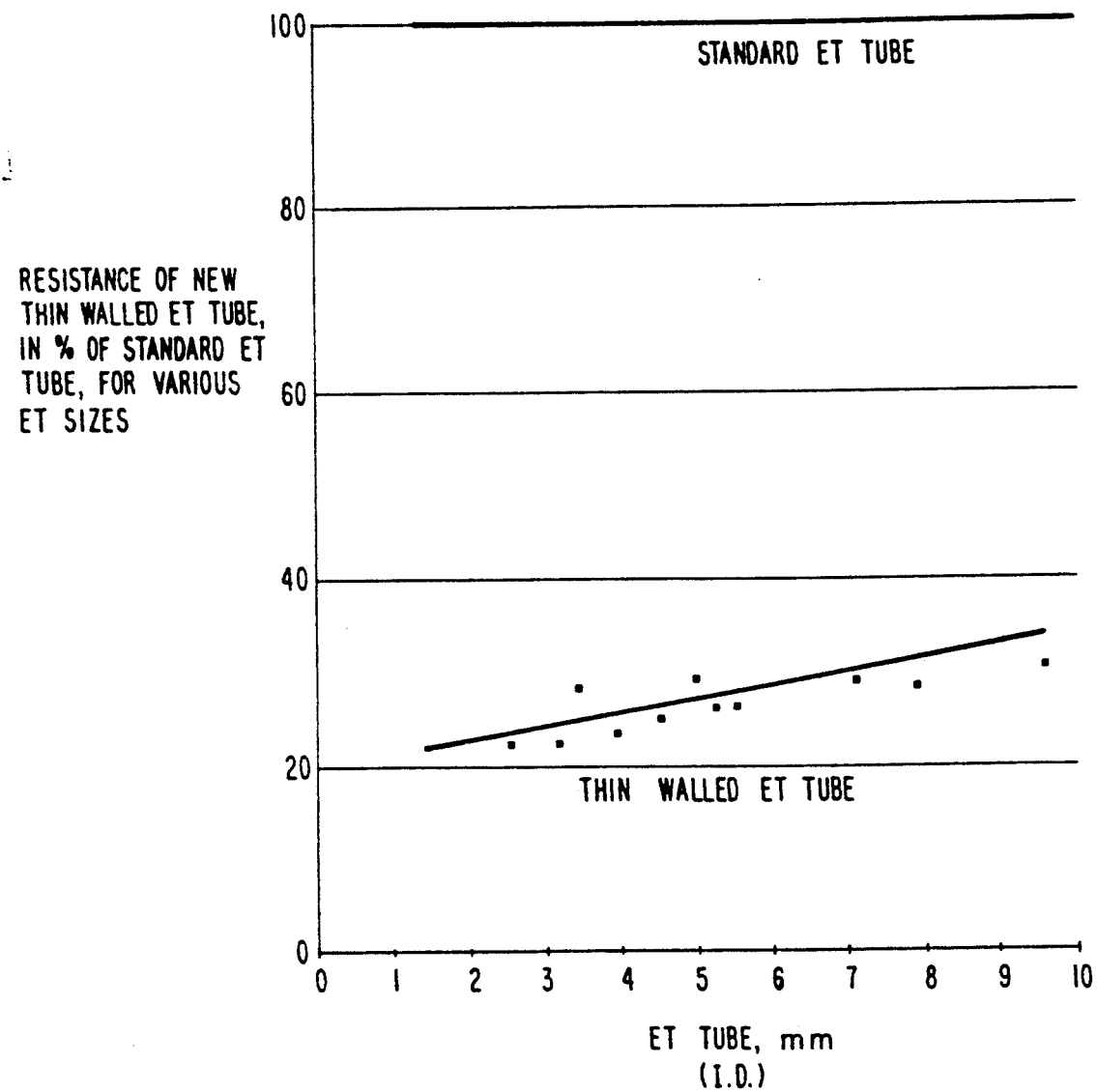
FIG. 4 shows a graph comparing air resistance in the inventive ultra thin walled endotracheal tube as compared to prior art endotracheal tubes.

With reference now to FIG. 4, a graph is depicted which compares standard endotracheal tubes such as those depicted in FIG. 2A and 3A with the ultra thin walled wire reinforced tubing of the present invention having a wall thickness of approximately 0.25 millimeters or 0.0098 in. The graph compares the resistance of the inventive thin walled endotracheal tubing as a percent of the air resistance of the standard endotracheal tubing for a range of endotracheal tubing based upon inner diameters. As can be seen from the graph in FIG. 4, the inventive thin walled endotracheal tubing results in a substantial decrease in resistance as compared to prior art endotracheal tubing. Also, the construction of the instant invention allows tubes with an inner diameter starting from about 1.5 mm, as shown in FIG. 4, and concomitantly having and outer diameter appreciably less than 5 mm. In addition, air flow resistance is further lowered for smaller sized endotracheal tubes which provides reduced air resistance in endotracheal tubing adapted for newborn patients.

Figure 5:
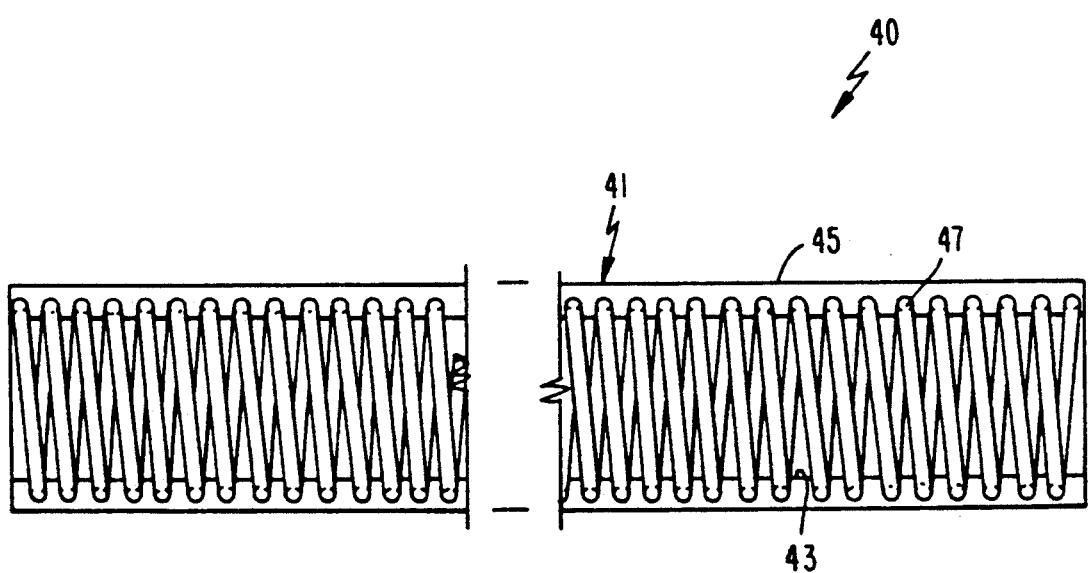
FIG. 5 shows an exemplary ultra thin walled wire reinforced endotracheal tube showing the spring material incorporated in the endotracheal tubing wall.

With reference now to FIG. 5, an exemplary ultra thin walled wire reinforced endotracheal tubing is generally designated by the reference numeral 40. The thin walled wire reinforced endotracheal tubing includes a tubing wall 41 having an inner surface 43 and outer surface 45. Incorporated within the tubing wall 41 is a spring 47. The diameter of the spring material 47 is sized in conjunction with the applied layers of polymeric material to provide the minimum wall thickness while maintaining sufficient strength to permit handling of the endotracheal tube. As disclosed above, a wall thickness of about 0.25 millimeters is attainable using the inventive method and apparatus for making the ultra thin walled wire reinforced endotracheal tubing. The wall thickness of about 0.25 mm is a preferred thickness with the wall thickness ranging between about 0.1 mm and 0.5 mm. A preferred range for the wall thickness includes between about 0.15 (0.0059 in) and 0.35 mm (0.0138 in). For a given wall thickness of 0.25 millimeters, it should be understood that the diameter of the wire spring material is less than the wall thickness to provide a polymeric layer along the inner and outer surfaces, 43 and 45 respectively of the tube 40. Alternatively, the wire spring material when positioned on the cylindrical mandrel prior to deposition of polymeric material may form part of the inner surface 43 of the tubing 40.

The apparatus and method of making the ultra thin walled wire reinforced endotracheal tubing provides a endotracheal tube having a thin wall thickness not attainable in prior art endotracheal tube making apparatus or method. The inventive apparatus and method also provide flexibility in adapting the manufacture of the inventive endotracheal tubing for various configurations for operating conditions such as an eccentric or slightly out of round mandrel. By having the nozzle of the metering pump 9 float or follow the contour of the mandrel, any slight out of roundness and/or eccentricity of the mandrel can be easily accommodated without effecting the quality of the tube.

In addition, the method of applying the polymer solution along the length of the mandrel permits programming of the control means to achieve different tubing configuration. For example, by increasing the flow rate of the dissolved polymer or reducing the rotation of the mandrel in conjunction with controlling the travel of the nozzle 11 along the mandrel, varying thicknesses of wall tubing may be obtained. By programming of more layers of different thicknesses on different parts of the mandrel, utilizing the control means, tapered endotracheal tubes may be manufactured. Alternatively, the mandrel 1 may be made having a tapered configuration wherein a tapered spring material may be used in conjunction with a uniform coating to produce a tapered tube having a uniform wall thickness.

Figure 6B:
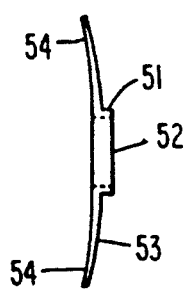
FIG. 6B is a cross sectional view of the sealing means of FIG. 6A.
Figure 6A:
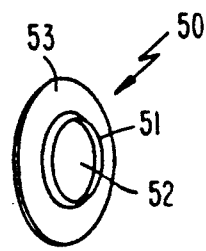
FIG. 6A is a perspective view of a sealing means according to one embodiment of the present invention.
Figure 7:
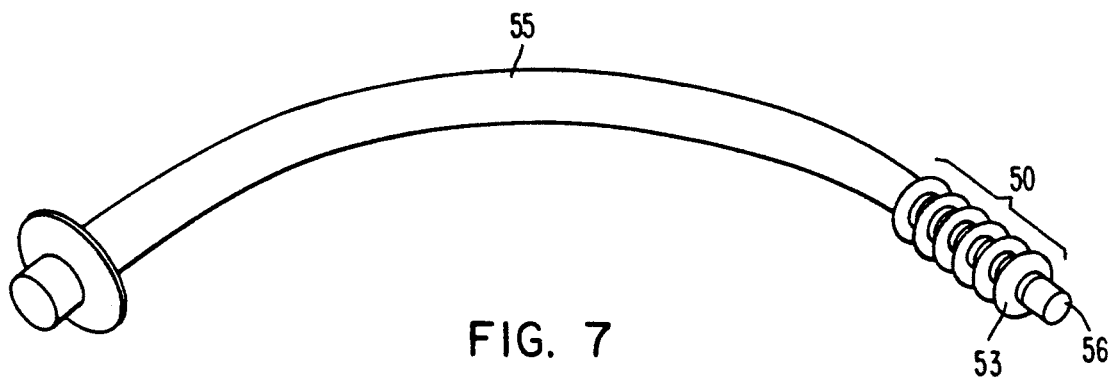
FIG. 7 shows an endotracheal tube according to one embodiment of the present invention which includes the sealing means of FIG. 6A.

FIG. 6A shows a sealing means 50 according to one embodiment of the present invention. As shown, the sealing means 50 is a gilled- or flanged-collar. The collar portion 51 includes a through-bore 52 which allows a tubular member to be inserted within the sealing means 50 and fixed thereto as shown in FIG. 7. The gill or flange 53 of the sealing means 50 is a thin, soft, pliable element made of a suitable biocompatable plastic material such as polyvinyl chloride, silicon rubber, polyethylene or the like, and is preferably integral with the collar portion 51, which may be made of a similar plastic material.

In a preferred embodiment, the gill or flange 53 of the sealing means 50 is made of a thin, e.g., 0.002 inches plasticized vinyl sheet, vacuum formed, and then cut and punched to an appropriate size. Other suitable methods of fabricating the sealing members, such as injection molding, separately fabricating and attaching the collar and flange portions, etc. could also be utilized. The thickness of the gill or flange portion should be relatively thin to ensure that the gill or flange is suitable soft and pliable. According to one embodiment of the present invention, the gills or flanges were as thin as about 0.0005 inches. In another embodiment the gills or flanges were between about 0.001–0.002 inches thick. While the thickness of the gills or flanges can be greater than 0.002 inches, depending on the pliability of the material from which they are formed, the limiting factor on this thickness is the ability of the gills or flange portions to provide the desire seal discussed above.

FIG. 6B show a cross section of the seal means of FIG. 6A. As shown, the gill or flange 53 extends from collar portion 51. The cross sectional area of the gill or flange 53 is tapered as illustrated so as to be thicker near the collar 51. The free edge 54 of the gill or flange 53 is feathered as shown. The gill or flange 53 may extend perpendicular from the collar 51 either straight or with a slight curve. The curved shape of the gill or flange 53 which is illustrated in FIG. 6B may provide a better seal when a tubular member having curved gills or flanges 53 is first inserted then backed out a short distance to reverse the curve of the gills or flanges 53 from the direction in which they are oriented when being inserted. In this embodiment, the curve shape can provide a small bias force to the seal means.

For an endotracheal tube, the diameter of the gills or flange portions can range from as small as 0.02 inches to 0.200 inches. The diameter or the gills or flanges can be determined from the outside diameter of the tubular member and the inner diameter of the lumen.

According to one design, the diameter of the gills or flanges as measured from the collar to the free end is between about 0.5–1.5 mm. The thickness of the gills or flanges at the collar is about 0.06 mm and the feathered edge is about 0.025 mm thick.

FIG. 7 shows an endotracheal tube 55 having the sealing means 50 of FIG. 6A attached thereto. As shown, the sealing means 50 are located near the distal end 56 of the endotracheal tube 55. In FIG. 7, six sealing members are shown on the endotracheal tube 55. However, it is noted that any number of sealing means including one, ten, twenty, thirty or more could be utilized.

Figure 8:
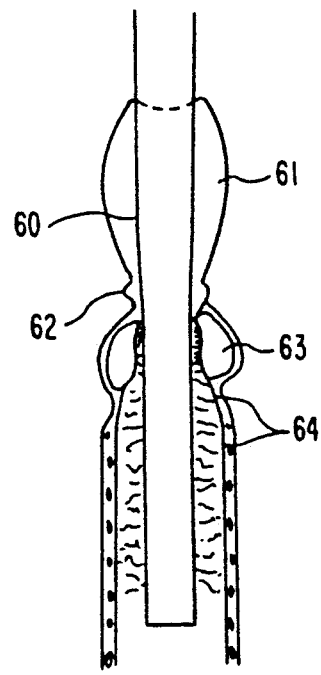
FIG. 8 shows an endotracheal tube with a sealing means according to the present invention positioned in a larynx-trachea.

FIG. 8 shows an endotracheal tube according to the present invention which is positioned in a larynxtrachea. As shown in FIG. 8 the endotracheal tube 60 is inserted through the epiglottis 61, vocal cord area 62 and the cricoid 63. The gills or flanges 64 of the sealing means (collars are not shown) which are located within the narrow or constricted portion of the lumen adjust to the inner diameter of this portion of the lumen due to their pliability and form a seal between the endotracheal tube 60 and the inner wall of the lumen.

It has been found that the gills or flanges will accommodate the anatomy of the trachea and that some tracheal bronchial secretions are likely to be entrapped between the gills or flanges, thus assisting sealing off air-/oxygen leakage. More importantly, there is almost negligible pressure on the adjacent epithelium of the trachea. This greatly reduces or eliminates tracheal wall injury. It is further noted that the tapering of the gills or flanges as discussed above helps protect the tracheal epithelium from possible undue physical trauma.

As can be understood from FIG. 8, the diameter of the gills or flanges 64 of the sealing means should be slightly larger than the distance between the outer wall of the tubular member 60 and the inner wall of the lumen. Accordingly, for a given lumen diameter, the diameter of the gills or flanges as measured above will be smaller for larger diameter tubular member and larger for smaller tubular members.

The sealing means of the present invention can utilize in conjunction with any tubular member which is designed to be sealing positioned in a lumen. For example, the sealing means may be utilized in conjunction with endotracheal tubes, ureteral catheters, and other similar tubes.

The sealing means of the present invention have a particular advantage in that they can be utilized in conjunction with endotracheal tubes which are less than about 5 mm in diameter. Heretofore, no sealing means, e.g. inflatable cuffs, was provided for such small endotracheal tubes. Of course, in addition to being particularly useful for small (less than about 5 mm) diameter endotracheal tubes, the sealing means of the present invention could also be suitable sized and utilized with larger diameter tubes.

The sealing means of the present invention has been found to be especially useful in conjunction with the above-discussed ultra thin wall walled wire reinforced endotracheal tubes. This combination provides endotracheal tubes which have low airway resistance and a maximum inside diameter for a given outside diameter. By utilizing the sealing means of the present invention in stead of inflatable cuffs on these ultra thin walled endotracheal tubes, possible deformation of the tubes caused by inflating or over inflating of the cuffs can be avoided. Moreover, as in the case of any type of endotracheal tube, use of the sealing means of the present invention in place of inflatable cuffs avoids the need for additional fluid passages needed to inflate and deflate the cuffs, thus allowing reduction of the overall diameter of the tubes.

Although the present invention has been described with reference to particular means, materials and embodiments, from the foregoing description, one skilled in the art can ascertain the essential characteristics of the present invention and various changes and modification may be made to adapt the various uses and characteristics thereof without departing from the spirit and scope of the present invention as describe in the claims which follow.

What is claimed is:

1. An endotracheal tube comprising a tubular member and a sealing means on said tubular member, said sealing means including a circular collar portion having a through hole centrally located therein and a pliable flange attached to an outer circumferential surface of said circular collar portion, said pliable flange being continuous along the entire circumferential surface of said circular collar portion and having a thickness of less than about 0.002 inches, said pliable flange providing a means to collect tracheal bronchial secretions and thereby assist in sealing said endotracheal tube in a tracheal when inserted therein.

2. An endotracheal tube according to claim 1, wherein said tubular member has an end and said sealing means is provided on said tubular member adjacent said end.

3. An endotracheal tube according to claim 1, wherein a plurality of said sealing means are provided on said tubular member.

4. An endotracheal tube according to claim 1, wherein said circular collar and said pliable flange are made from a polymeric material.

5. An endotracheal tube according to claim 1, wherein said tubular member has an outer diameter which is less than about 5 mm.

6. An endotracheal tube according to claim 1, wherein said pliable flange has a free edge and a thickness which is greater near said circular collar portion than said free edge so as to be tapered.

7. An endotracheal tube according to claim 6, wherein said pliable flange has a thickness between about 0.002 to 0.0005 inches.

8. An endotracheal tube according to claim 6, wherein said free edge of said pliable flange is feathered.

9. An endotracheal tube according to claim 1, wherein said tubular member is wire reinforced.

10. An endotracheal tube according to claim 9, wherein a plurality of said sealing means are provided on said tubular member.

11. An endotracheal tube according to claim 9, wherein said tubular member has an end and said sealing means is provided on said tubular member adjacent said end.

12. An endotracheal tube according to claim 9, wherein said pliable flange has a thickness between about 0.002 to 0.0005 inches.

13. An endotracheal tube according to claim 9, wherein said circular collar and said pliable flange are made from a polymeric material.

14. An endotracheal tube according to claim 9, wherein said pliable flange has a free edge and a thickness which is greater near said circular collar portion than said free edge so as to be tapered.

15. An endotracheal tube according to claim 14, wherein said free edge of said pliable flange is feathered.

* * * * *